United States Patent [19]

Greiner et al.

[11] Patent Number: 5,137,605
[45] Date of Patent: Aug. 11, 1992

[54] PROCESS FOR DEHYDRATION OF CONDENSATION REACTION MIXTURES OBTAINED BY AZEOTROPIC DISTILLATION

[75] Inventors: Istvan Greiner; Jeno Szilbereky; Bela Stefkó; Gyorgy Thaler, all of Budapest, Hungary

[73] Assignee: Richter Gedeon Vegyeszeti Gyar Rt., Budapest, Hungary

[21] Appl. No.: 598,404

[22] Filed: Oct. 15, 1990

Related U.S. Application Data

[63] Continuation-in-part of Ser. No. 412,109, Sep. 25, 1989, abandoned.

[30] Foreign Application Priority Data

Sep. 26, 1988 [HU] Hungary .............................. 5006/88

[51] Int. Cl.$^5$ .............................................. B01D 3/36
[52] U.S. Cl. ........................................ 203/14; 203/67; 203/69; 203/87; 203/98
[58] Field of Search ...................... 203/14, 69, 68, 67, 203/DIG. 21, 87, 98

[56] References Cited

U.S. PATENT DOCUMENTS

| | | | |
|---|---|---|---|
| 1,862,706 | 6/1932 | Ricard et al. | 203/14 |
| 2,043,178 | 7/1936 | Carney | 203/14 |
| 2,362,093 | 11/1944 | Pyzel et al. | 203/14 |
| 3,663,631 | 5/1972 | Takeya et al. | 203/87 |
| 3,669,847 | 6/1972 | Feder et al. | 203/14 |
| 3,687,819 | 8/1972 | Levin | 203/14 |
| 3,855,077 | 12/1974 | Bieser et al. | 203/87 |
| 4,115,208 | 9/1978 | Verstegen | 203/14 |

FOREIGN PATENT DOCUMENTS

| | | | |
|---|---|---|---|
| 2359205 | 6/1974 | Fed. Rep. of Germany | 203/14 |
| 3216262 | 12/1982 | Fed. Rep. of Germany | 203/14 |
| 1194137 | 4/1958 | France | 203/14 |

*Primary Examiner*—Virginia Manoharan
*Attorney, Agent, or Firm*—Herbert Dubno; Jonathan Myers

[57] ABSTRACT

A process for the dehydration of substances, mixtures, primarily condensation reaction mixtures, (e.g. direct esterification, direct acetal formation, direct ketal formation), performed by continuous azeotropic distillation with an organic solvent forming with water an azeotropic mixture of minimal boiling point and unable to mix with water, carried out in such a way that the distillate is cooled at least to the temperature, at which the condensate with the given water content or the organic phase of the condensate is just supersaturated with respect to water, and the organic phase of lower water content obtained in this way is recycled to the distilling boiler. The organic solvents used are e.g. benzene, toluene, 1,2-dichloroethane, chloroform, carbon tetrachloride.

3 Claims, 2 Drawing Sheets

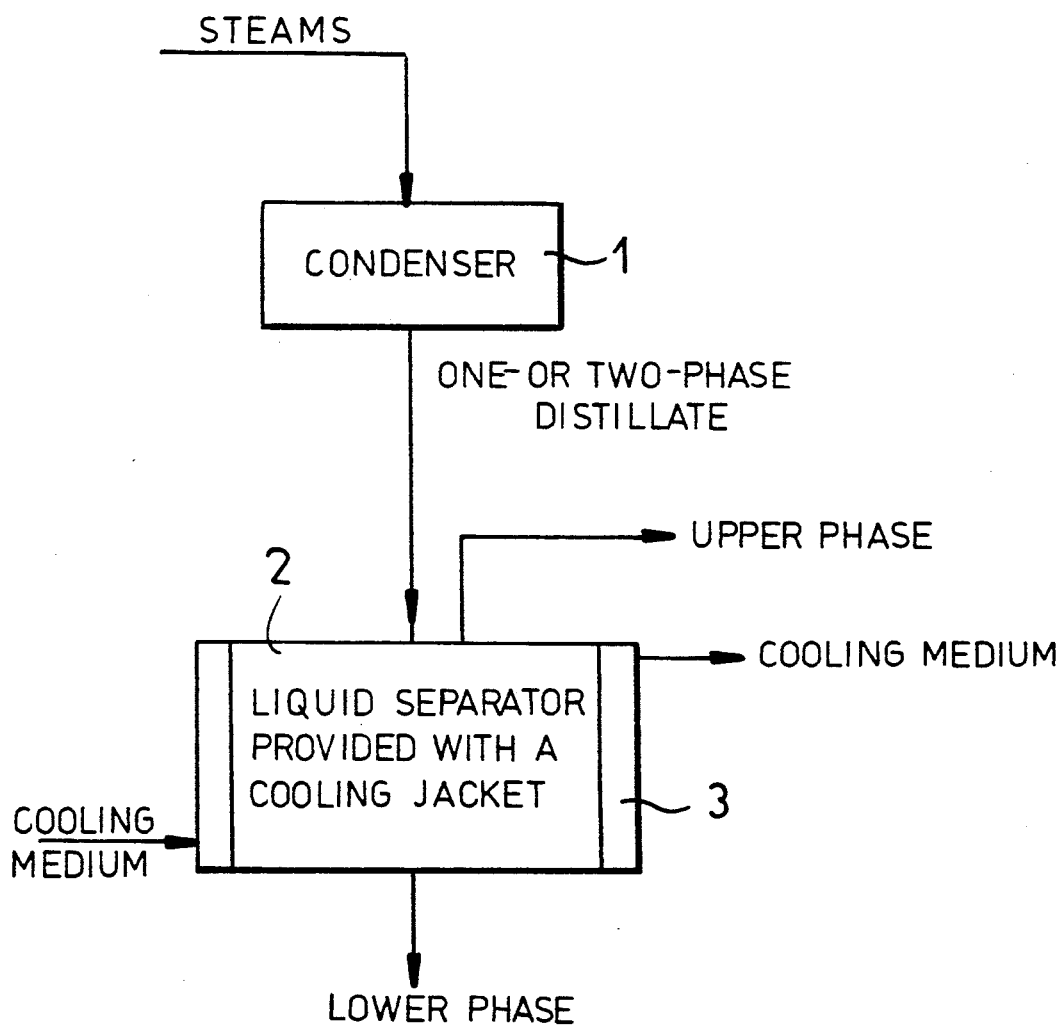

PROCESS FOR DEHYDRATION OF CONDENSATION REACTION MIXTURES OBTAINED BY AZEOTROPIC DISTILLATION

CROSS REFERENCE TO RELATED APPLICATIONS

This application is a continuation-in-part of Ser. No. 07/412,109 filed Sep. 25, 1989, now abandoned.

FIELD OF THE INVENTION

The present invention relates to a process for the dehydration of substances, mixtures, primarily condensation reaction mixtures, obtained by continuous azeotropic distillation with an organic solvent, forming with water an azeotropic mixture of a minimal boiling point and unable to mix with water.

BACKGROUND OF THE INVENTION

In many fields of the chemical industry there is a need for dehydration. The most important among them is the continuous dehydration of reaction mixture originating from reactions resulting in the liberation of water. The most characteristic representatives of the condensation reaction are direct esterification (the reaction of an organic acid or acid anhydride and an alcohol), direct amidation (the reaction of an organic acid or acid anhydride and an amine) and formation of an acetal or ketal (the reaction of an aldehyde or ketone and an alcohol). The continuous removal of water from the reaction mixture during progression of these kinds of reactions pushes the reaction equilibrium in the direction of product formation.

On an industrial scale water is continuously removed from the reaction mixture by extraction or by azeotropic distillation. The essence of the extraction is to add an organic solvent, which practically does not mix with water, to the reaction mixture, this way the water forming during the reaction separates in a new phase from the reaction medium. This manner is reported in the literature, c. f. e. g. J. Am. Chem. Soc., 70, 3135 (1948) and J. Pharm. Pharmacol. 2, 119 (1950). The removal of water by azeotropic distillation is carried out in such a way that an organic solvent, which forms an azeotropic mixture of minimal boiling point with water but does not mix with water, is added to the reaction mixture, and the vapors forming during boiling of the reaction mixture are condensed separately from the reaction zone, and from the two phases separating from the distillate the one more rich in the organic solvent, containing just a small amount of water, is recirculated to the reaction mixture.

A batch-wise azeotropic distillation method for the removal of water is described in the German patent specification No. 3,335,312. According to this method, organic solvents freely mixing with water are used. The disadvantage of the method is that the regeneration of these solvents is difficult, a rectification column is needed for the dehydration of the solvent. This makes the procedure complicated and expensive.

Water removal carried out by azeotropic distillation was also carried out using organic solvents both lighter and heavier than water. From among the solvents lighter than water, benzene, toluene and diisopropyl ether can be used advantageously (c.f.: Deák, Gy.: "Szerves vegyipari alapfolyamatok kézikönyve" (Handbook of the Basic Processes of Organic Chemistry—in Hungarian), 455 (1978), and DEA-29,17,087). Also many examples are known from the literature for the application of organic solvents heavier than water, for example carbon tetrachloride or 1,2-di-chloroethane (Org. Synt. Coll. Vol. I. 261 (1955and the U.S. Pat. No. 2,010,426).

Water removal carried out by azeotropic distillation is used still for dehydration of substances and mixtures (Kirk-Othmer: Encyclopedia of Chemical Technology, Azeotrop Distillation; III. Edition, Wiley-Interscience (1976)).

The disadvantage of the azeotropic distillation methods described above is that the water resulting from the reaction cannot be removed to such an extent that the given equilibrium reaction is complete from the point of view of the product.

Compared to the azeotropic distillation method, the extractive method is still less advantageous, because the extent of water removal reached is even lower than that reached by the known azeotropic distillation methods.

The most frequent application area of water removal, carried out by azeotropic distillation is direct esterification. From the point of view of water removal, in this case—and in the case of direct acetal and ketal forming—one more disadvantageous factor occurs.

In the reactions mentioned above often the 3-5-fold excess of such alcohols of short carbon chain, mostly of 1-4 carbon atoms is used as reactant, the boiling point of which is close to the boiling point of the solvent forming an azeotropic mixture of minimal boiling point with water, and practically not mixing with water. Because of the close value of the boiling points, a significant amount of the alcohol distills over with the azeotropic mixture, and this results in a significant dissolution between the separating phases in the condensate.

In many cases there is a need for a higher degree of dehydration than that attainable by using the known processes. This task occurs mostly at those equilibrium reactions, in which the value of the equilibrium constant is around one, or the equilibrium is shifted towards the hydrolysis, that is, opposite to the desired reaction. This is the situation, for example, in the esterification of piruvic acid, oxalic acid, ethylmalonic acid or phthalic acid, and the amidation of formic acid. In this case dehydration is carried out by recirculating the refluxing organic phase, removed from the reaction mixture by distillation, through a solid desiccant, e.g. $CaCl_2$, $P_2O_5$, $K_2CO_3$, back to the reaction mixture (Org. Synth. Coll. Vol. I., 261 (1955)).

According to the method described in J. Org. Chem. 48, 3106 (1983) the reaction mixture is passed through a column filled with a solid desiccant and the low water concentration necessary for the favorable chemical transformation is produced this way.

On an industrial scale, the application of solid desiccants has the disadvantage that a huge amount must be used, and the regeneration of the desiccant is difficult, too. These factors make the realization of the reaction difficult and expensive.

OBJECT OF THE INVENTION

The object of the invention is to provide a continuous water removal process which is better, simpler and cheaper than the processes known for the removal of water from substances, mixtures and primarily condensation reaction mixtures. In the case of condensation reactions, a further goal of the water removal is to shift the equilibrium to the direction of product formation, that is, to increase the yield of the product.

SUMMARY OF THE INVENTION

The invention is based on the recognition that in the case of dehydration carried out by azeotropic distillation, the water content of substances, mixtures and primarily condensation reaction mixtures can be reduced below the water content attainable by the known azeotropic distillation if the azeotropic distillation is conducted in such a way that the condensate with the given water content, incidentally forming a new phase close to the boiling point, is cooled to the temperature where the organic solvent, forming with water an azeotropic mixture of minimal boiling point and being practically unable to mix with water, becomes supersaturated with respect to the water. Because of this step, further water separation occurs, and an organic phase with a lower water content can be recycled into the distillation boiler.

Specifically, the invention relates to a process for dehydrating an azeotropic mixture obtained during an azeotropic distillation process, said azeotropic mixture containing water and an organic solvent which forms with water an azeotropic mixture of minimal boiling point, and which is unable to mix with water, which consists essentially of the steps of:

(a) condensing the azeotropic mixture at a temperature just below its boiling point to form a distillate containing either a one-phase liquid wherein the water is dissolved in the organic solvent if the water content of the distillate is too low to form a separate aqueous phase or a two-phase liquid containing both an aqueous phase and an organic phase, wherein the organic phase contains both the organic solvent and water, if the water content of the distillate is sufficiently high to form a separate aqueous phase;

(b) cooling the one-phase distillate or the organic phase of the two-phase distillate to a temperature where the organic solvent, forming an azeotropic mixture with water of minimal boiling point and being practically unable to mix with water, becomes supersaturated with respect to the water, to separate same into two new phases which include a new organic phase rich in the organic solvent and having a lower water content than that of either the one-phase liquid or the organic phase of the two-phase liquid, defined in step (a), and a new aqueous phase; and (c) recycling the new organic phase rich in the organic solvent having a lower water content to the azeotropic distillation process.

BRIEF DESCRIPTION OF THE DRAWING

The above and other objects, features and advantages of the present invention will become more readily apparent from the following description, reference being made to the accompanying drawing in which.

On the phase diagram, $x_{ext}$ and $x_{az}$ mean the water concentrations obtainable by the extractive method and by azeotropic distillation, respectively.

When water is removed by extraction, the water content of the reaction mixture cannot be reduced below the $x_{ext}$ water concentration value, because this water concentration corresponds to the water concentration of the organic phase being in equilibrium with the water phase at the boiling point (Point B). In the case of a lower water content the organic phase and the water do not separate into two phases.

When water removal is carried out by conventional azeotropic distillation, the water content of the reaction mixture cannot be reduced below the $x_{az}$ value, because by condensing the vapor phase of a reaction mixture of this composition, Point B is reached on the diagram, where the liquid state distillate does not separate into two phases. This means that more water cannot be removed from the condensed vapor, and the total amount of water is recirculating to the reaction mixture.

Figure 2:
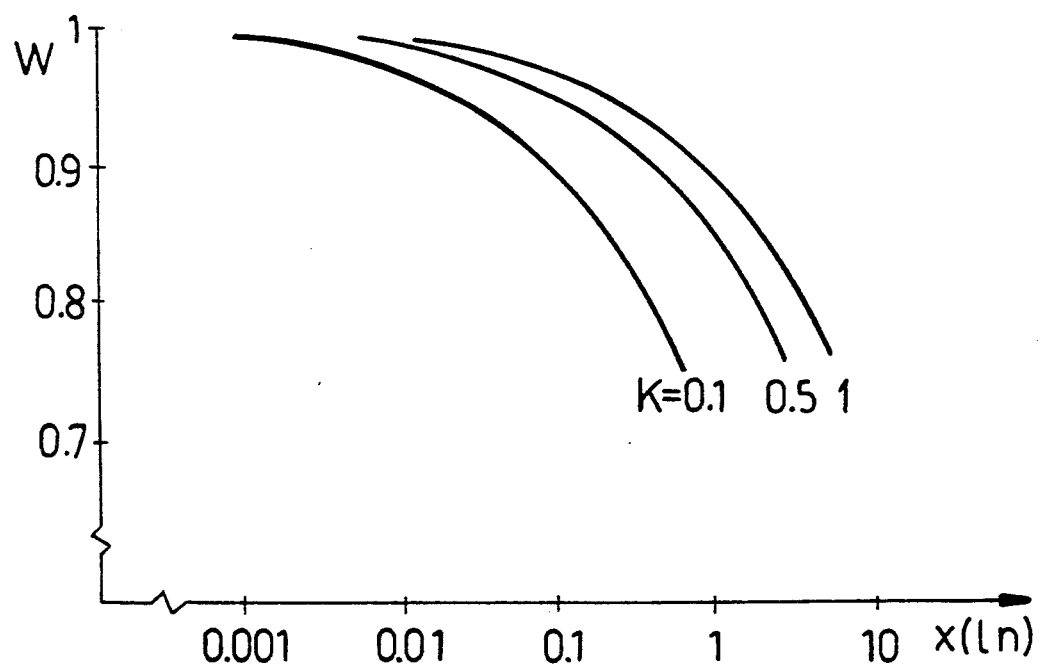

FIG. 2 is a graph showing the theoretical yield (w) of a given product of a condensation reaction plotted on the Y axis against the water content in the reaction mixture expressed in mol(%) plotted on the X axis, and;

FIG. 3 is a flow diagram describing the stages of dehydrating an azeotropic mixture containing water and an organic solvent to obtain said organic solvent having a lower water content.

DETAILED DESCRIPTION OF THE DRAWINGS

Figure 1:
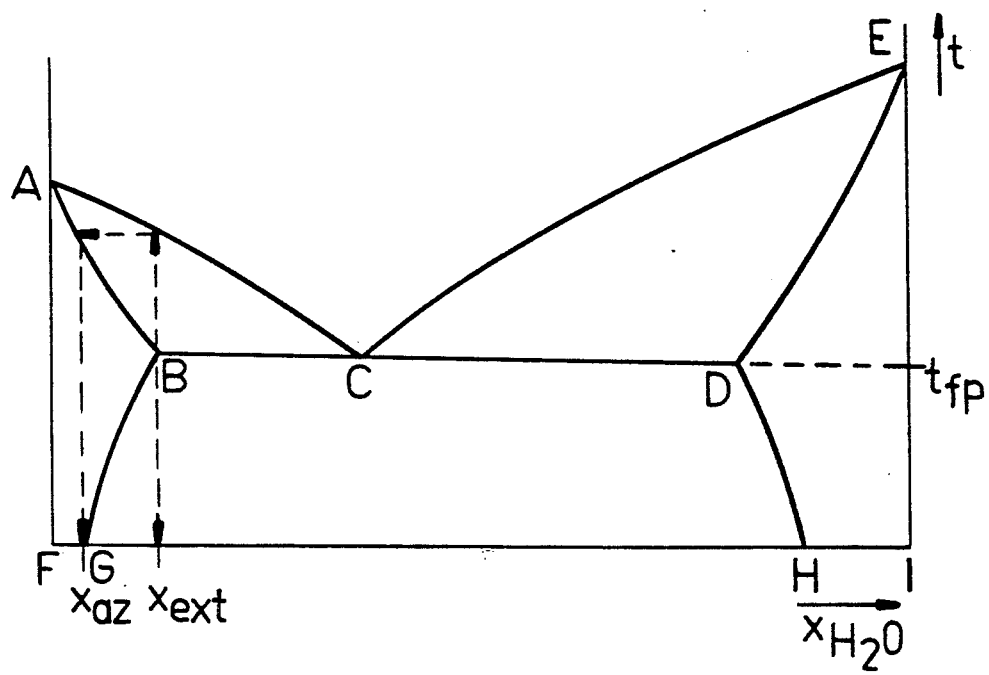
FIG. 1 ia a phase diagram of a two-component system, which contains water and an organic solvent practically not mixing with water, but which forms an azeotropic mixture with water of a minimal boiling point.

In the phase diagram which is FIG. 1 the ACE curve is designated as the vapor curve and the ABDE curve as the liquid curve. Above the vapor curve the mixtures of water and organic solvent are in the gas phase, and of course they are one phase mixtures at all molar ratios since gases are miscible with one another without limitation. The area under the liquid curve is divided into 3 parts. The mixtures belonging to the area designated GBDH are in a two-phase stage. The mixtures belonging to the AFGB and EDHI areas are in one phase stages. Thus if a benzene-water azeotropic mixture were described in the flow diagram of FIG. 1, then one of these areas, namely AFGB shows the water-dissolved-in-benzene mixture and the other area, namely EDHI shows the benzene-dissolved-in-water mixture. The BG and DH curves give the solubility limits of the components in the liquid phase.

Boiling the two phase mixture shown by the GBDH area, the molar ratio of the vapor is the value according to point C in every case. When this vapor is condensed, two phases are obtained: one of them has the molar ratio according to point D, and the other has the molar ratio according to point B.

In the flow diagram which is FIG. 3 the process for dehydrating an azeotropic mixture obtained following an azeotropic distillation is described.

An outlet mixture leaving an azeotropic distillation process designated as "steams" and consisting of water vapor and a vaporized organic solvent partially miscible with water and which is capable of forming an azeotropic mixture with water is led into a condenser 1.

In the condenser the mixture is cooled to a temperature just below its boiling point to form a distillate containing either a one phase liquid wherein the water is dissolved in the organic solvent if the water content of the distillate is too low to form a separate aqueous phase or a two phase liquid containing both an aqueous phase and an organic phase, wherein the organic phase contains both the organic solvent and water, if the water content of the distillate is sufficiently high to form a separate aqueous phase.

The one phase distillate or the organic phase of the two phase distillate cooled in the previous step is then transferred to and cooled down significantly further in a liquid separator 2 provided with a cooling jacket 3 to a temperature where the organic solvent, which forms an azeotropic mixture with water at a minimal boiling point and being practically unable to mix with water, comes supersaturated with respect to the water. As a result said one- phase distillate or said organic phase of the two-phase distillate forms two new phases which include a new organic phase rich in the organic solvent and having a lower water content than that of either the one-phase liquid or the organic phase of the two-phase liquid and a new aqueous phase.

The cooling jacket contains a liquid cooling medium which brings down the temperature of the distillate from just below its boiling point to a point where the organic solvent becomes supersaturated with water. For instance when the organic solvent is benzene, the temperature is brought down to about 6° C.

The new organic phase rich in the organic solvent and with a very low water content is then separated from the new aqueous phase. Where benzene is the organic solvent, the new organic phase is above the new aqueous phase since benzene has a lower density than water. Thus benzene is the upper phase and water is the lower phase. When 1,2-dichloroethane is the organic solvent, then it is the aqueous phase that is the upper phase and the organic phase is the lower phase.

The organic phase with the reduced water content is then recycled back to the azeotropic distillation process.

The reduction of water in the product is significant especially in the range of water concentration marked on FIG. 1 by point B and below that, because with the known azeotropic distillation method, where the separating phases of the distillate are not cooled, it is theoretically impossible to reach lower water concentration than the one marked by $x_{az}$ in FIG. 1.

By dehydrating the reaction mixtures of direct esterification, acetal and ketal formation, it was also recognized that if a solvent forming an azeotropic mixture of minimal boiling point with water, not mixing with water, and having a higher density than water, is used, then the amount of alcohol used as reactant can be reduced close to the theoretically necessary amount. The reason is that the organic solvent continuously takes up the alcohol dissolved in the aqueous phase during the reaction, and in this way the alcohol is recycled with the organic phase into the reaction medium. This way the reciprocal increase in solubility, caused by the alcohol, disappears or at least decreases.

Thus, the object of the invention is a process for dehydration of substances, mixtures, primarily condensation reaction mixtures, by continuous azeotropic distillation with an organic solvent forming with water an azeotropic mixture of minimal boiling point and unable to mix with water, characterized in that the distillate is cooled at least to the temperature where the condensate with the given water content, or the organic phase of this condensate is just supersaturated in respect of water, and the resulting organic phase with low water content is recycled into the distilling boiler.

In the process according to the present invention, the distillate is cooled suitably to the temperature where from the separating phases the one recycled into the reaction mixture is still in a liquid state, that is down to the melting point of the organic phase supersaturated with water.

The process according to the present invention can be advantageously realized in the case of the condensation reactions leading to equilibrium, where the superior water removal results in an increase of the yield.

Especially good results can be reached at those condensation reactions, where the value of the equilibrium constant (K) is one or less than one. FIG. 2 shows that the theoretical yield (w) concerning the product (C) of the condensation reaction characterized by the $$A + B = C + H_2O$$

general scheme, even in the case of low water content values (x is the water content of the mixture in mol %) is significantly changing.

For example, if the water content in the reaction mixture is reduced, using the process according to the present invention, to 0.02 mol %, as opposed to the 0.2 mol % reached by the known procedures, then this results in a theoretical yield increase of 4 to 10% in the case of reactions having an equilibrium constant of one or less than one.

In those condensation reactions, where one of the reactants is a short chained alcohol, the known procedures use a 3 to 5-fold excess of the alcohol in order to shift the reaction into the direction of product formation. From the point of view of dehydration, the alcohol excess has the disadvantage mentioned above, that is, it increases the solubility of water in the solvent used for azeotropic distillation. Using the process according to the present invention, it is possible to reduce the amount of alcohol, with simultaneous increase of conversion, close to the theoretically necessary amount (about 5-10 mol % excess).

According to the process of the present invention, the solvent not mixing with water can be both of higher density than water, preferably 1,2-dichloroethane, chloroform or carbon tetrachloride, and of lower density than water, preferably benzene or toluene.

The process according to the present invention is illustrated by the following nonlimiting examples.

The literature sources of the yield data reported in the examples for comparison are summarized in the following (1) J. Chem. Soc., 532 (1948) (extractive method, using benzene).
(2) J. Am. Chem. Soc., 70, 3135 (1948) (extractive method).
(3) Annalen 571, 53, (1951) (extractive method, the reproduction of the procedure of (2).
(4) Org. Synth. Coll. Vol. III., 610 (1955) (azeotropic method using benzene).
(5) J. Am. Chem. Soc., 66, 1657 (1944) (azeotropic method using carbon tetrachloride).
(6) Org. Synth. Col. Vol. I., 261 (1955) (azeotropic method using carbon tetrachloride, drying with $K_2CO_3$).
(7) J. Pharm. Pharmacol., 2, 229 (1950) (extractive method).
(8) U.S. Pat. No. 2,010,425 from 1935 (azeotropic method using 1,2-dichloroethane).
(9) DE-A 29 17 087 from 1979 (azeotropic method using diisopropyl ether).
(10) Bulletin de la Societe Chimique de Belgique, 28, 339 (1922) (extractive method).

EXAMPLE 1

66 g. of ethylmalonic acid are dissolved in a mixture of 200 ml. of benzene and 64 g. of methanol. 0.5 ml. of concentrated sulphuric acid are added to the reaction mixture. It is refluxed for 10 hours through a water separating unit. The distillate collected in the unit is cooled to 6° C. After the reaction, the reaction mixture is quickly neutralized by adding 34 ml. of a 5% by weight icy aqueous sodium hydrogencarbonate solution. The organic phase is dried and distilled fractionally.

54 g (67.5%) of dimethyl ethylmalonate are obtained, boiling point is 98° C. at a pressure of 3300 Pa.

Yield in the literature: 50% (1).

In Table I examples are summarized which demonstrate the yield increase reachable by dehydration in the case of esterification reactions. Table I contains the parameters of the process, and the yield data of esterification reactions measured and known from the literature respectively.

Esterification is carried out as follows:

1 mole of a carboxylic acid or anhydride is dissolved or suspended in the mixture of 1,2-dichloroethane and, based on the amount of the acid or anhydride, an alcohol in an excess of 10 mol % is added. If necessary a catalyst is added to the reaction mixture, and the mixture is refluxed for 12 hours through a cooled water separating unit. The reaction mixture is quickly neutralized with icy 5% by weight aqueous sodium hydrogencarbonate solution, used in an amount corresponding to the theoretically necessary amount, the organic phase is dried and fractionally distilled.

TABLE I

| No. of the example | Product | Catalyst | Cooling temperature | Yield measured | Yield literature |
|---|---|---|---|---|---|
| 2 | dimethyl ethyl-malonate | cc. sulphuric acid | 10° C. | 85–88% | 50% (1) |
| 3 | methyl pyruvate | PTSA | 5° C. | 78–82% | 73% (2) 59% (3) 65–71% (4) |
| 4 | ethyl pyruvate | PTSA | 5° C. | 77–82% | 59% (5) |
| 5 | diethyl oxalate | — | 10° C. | 93–95% | 80–85% (6) 48–51% (7) |
| 6 | dibutyl phthalate | cc. sulphuric acid | 10° C. | 98–99% | 96% (8) |

PTSA = p-toluene sulphonic acid

In Examples 2, 3, 4 and 5 the corresponding carboxylic acid is the starting material. The starting material of the product according to the Example 5 contains 2 moles of crystal water. The starting material in Example 6 is phthalic acid anhydride.

EXAMPLE 7

The mixture of 30 ml. of formic acid, 31 g. of aniline and 120 ml. of 1,2-dichloroethane is boiled for 12 hours using a water separating unit. The distillate collected in the unit is continuously cooled to 10° C. The product is isolated by fractional distillation from the reaction mixture previously neutralized with icy, 5% by weight aqueous sodium hydrogencarbonate solution.

39.2 g. of formanilide are obtained with a yield of 97%. The boiling point of the product is 124° C./200 pa, the melting point is 49°–50° C.

Literature data: yield 91.7%, boiling point 146° C./460 Pa, melting point 47°–48.5° C. (9).

EXAMPLE 8

The mixture of 36 g. of (0.5 moles) butyric aldehyde, 81.4 g. (1.1 moles) of n-butyl alcohol, 0.2 g. of p-toluene sulphonic acid and 250 ml. of 1,2-dichloroethane refluxed for 14 hours through a water separating unit. The distillate collected in the unit is constantly cooled below 10° C. The reaction mixture is extracted with a 5% by weight aqueous sodium hydrogencarbonate solution taken in excess, the organic phase is dried and fractionally distilled.

74.7 g. of dibutyl butanal are obtained with a yield of 74%. The boiling point of the product is 106°–112° C./2500 pa.

Literature data: yield 13%, boiling point 100°–106° C./2400 Pa, (10).

The advantages of the process of the present invention are the following:

a) the water content of the organic solvent forming with water an azeotropic mixture of minimal boiling point, but not mixing with water in the condensate is lower, and because of this in the azeotropic distillation apparatus, the water content can be significantly reduced, compared to the methods known;

b) the process can be used on an industrial scale, too, and the required apparatus is negligible;

c) after removal can be carried out in an environmental protective way in the case of condensation reactions;

d) because of the lower water content, 5–30 percent yield increase can be reached, based on the final product;

e) because of the lower water content of the refluxing organic phase, the water concentration is lower in the reaction mixture than with the earlier processes even until the formation of the equilibrium mixture, and as a result of this, the rate of hydrolysis will be lower during the reaction, and the reaction time will be significantly shorter;

f) in many cases significant energy saving can be reached with the shortening of reaction time;

g) the processing of the reaction mixture and the purification of the final product are significantly easier since as a result of the higher conversion, the amount of non-reacting materials is significantly less.

What is claimed is:

1. A process for dehydration of a condensation reaction mixture which consists essentially of the steps of:
    (a) azeotropically distilling a condensation reaction mixture containing a reaction product, water and an organic solvent which forms with water an azeotropic mixture of minimal boiling point and which is unable to mix with water, said azeotropic mixture consisting of water and the organic solvent, to remove said azeotropic mixture from the condensation reaction mixture;
    (b) condensing the azeotropic mixture at a temperature just below its boiling point to form a distillate containing either a one-phase liquid wherein the water is dissolved in the organic solvent when the water content of the distillate is insufficient to form a separate aqueous phase or a two-phase liquid containing both an aqueous phase and an organic phase, wherein the organic phase contains both the organic solvent and water, when the water content of the distillate is sufficient to form a separate aqueous phase;
    (c) cooling the one-phase distillate or the organic phase of the two-phase distillate to a temperature of about 5° to 10° C. where the organic solvent, forming an azeotropic mixture with water of minimal boiling point and unable to mix with water, becomes supersaturated with respect to the water, to separate same into two new phases which include a new organic phase rich in the organic solvent and having a water content of about 0.02 mole %, which is lower than that of either the one-phase liquid or the organic phase of the two-phase liquid, defined in step (b), and a new aqueous phase; and (d) recycling the new organic phase rich in the organic solvent having a water content of about 0.02 mole % to the azeotropic distillation process, such that a 5 to 30% yield increase can be reached based 2. The process defined in claim 1 wherein the organic solvent has a higher density than that of water and is a halogenated, aliphatic hydrocarbon, selected from the group consisting of 1,2-dichloroethane, chloroform and carbon tetrachloride.

3. The process defined in claim 1 wherein the organic solvent has a lower density than that of water and is an aromatic hydrocarbon, selected from the group consisting of benzene and toluene.

* * * * *

UNITED STATES PATENT AND TRADEMARK OFFICE
CERTIFICATE OF CORRECTION

PATENT NO.   :   5 137 605
DATED        :   11 August 1992
INVENTOR(S)  :   Istvan GREINER et al.

It is certified that error appears in the above-identified patent and that said Letters Patent is hereby corrected as shown below:

Col. 2, line 4, change "1955and"
                to -- 1955) and -- .

Col. 3, line 56, change "ia"
                 to -- is -- .

Col. 8, line 21, change "after"
                 to -- water -- .

Col. 9, add line 10 as follows:
        -- on a final product obtained. -- .

Signed and Sealed this

Fifth Day of October, 1993

Attest:

BRUCE LEHMAN

Attesting Officer                 Commissioner of Patents and Trademarks